(12) United States Patent
Al Barazanji

(10) Patent No.: US 6,380,155 B1
(45) Date of Patent: Apr. 30, 2002

(54) USE OF VASOPRESSIN RECEPTOR ANTAGONIST FOR REGULATION OF ACTH RELEASE

(75) Inventor: Kamal A Al Barazanji, Bishops Stortford (GB)

(73) Assignee: SmithKline Beecham plc., Brentford (GB)

( * ) Notice: Subject to any disclaimer, the term of this patent is extended or adjusted under 35 U.S.C. 154(b) by 0 days.

(21) Appl. No.: 09/563,870

(22) Filed: May 3, 2000

Related U.S. Application Data

(63) Continuation of application No. 09/155,188, filed as application No. PCT/EP97/01436 on Mar. 19, 1997, now abandoned.

(30) Foreign Application Priority Data

Mar. 22, 1996 (GB) .............................................. 9606016

(51) Int. Cl.$^7$ .............................................. A61K 38/11
(52) U.S. Cl. ............................. 514/2; 514/16; 530/315
(58) Field of Search ............................. 530/315; 514/2, 514/9, 11, 16

(56) References Cited

U.S. PATENT DOCUMENTS

| | | | | |
|---|---|---|---|---|
| 4,814,333 A | * | 3/1989 | Ravaris | ...................... 514/255 |
| 5,070,187 A | | 12/1991 | Gavras et al. | ............... 530/315 |
| 5,733,790 A | * | 3/1998 | Potter et al. | ................. 436/518 |
| 5,830,866 A | * | 11/1998 | Redei et al. | ................... 514/18 |

OTHER PUBLICATIONS

Lee et al. Effect of AVP and oxytocin on insulin release . . . Am. J. Physiol. vol. 269, pp. E1095–E1100, 1995.*

Pasquali et al. Hypothalamic–Pituitary–Adrenal Axis Activity . . . Metabolism, vol. 45, No. 3, pp. 351–356, Mar. 1996.*

Bernardini et al., Neuroendocrinology, 60(5), pp. 503–508 (1994).

Honda et al., Am. J. Physiol., 266, pp. R1448–R1453 (1994).

Evans et al., J. Endocrinol., 122(1), pp. 107–116 (1989).

Hader et al., Acta Endocrinologica, 123(6), pp. 622–628 (1990).

* cited by examiner

Primary Examiner—Jeffrey E. Russel
(74) Attorney, Agent, or Firm—Linda E. Hall; William T. King; Stephen A. Venetianer

(57) ABSTRACT

A method for normalising abnormally elevated ACTH release in mammals, such as humans, which method comprises the administration of an effective, non-toxic amount of a compound which regulates the biological activity of the arginine vasopressin V1b receptor (the AVP V1b receptor); a compound and composition for use in such method.

4 Claims, No Drawings

USE OF VASOPRESSIN RECEPTOR ANTAGONIST FOR REGULATION OF ACTH RELEASE

This is a continuation of application Ser. No. 09/155,188 filed Mar. 11, 1999; which is a 371 of International Application No. PCT/EP97/01436, filed Mar. 19, 1997, which claims priority from GB Application No. 9606016.5, filed Mar. 22, 1996.

The invention relates to a novel use and in particular to the use of compounds which regulate the biological activity of the arginine vasopressin V1b receptor (the AVP V1b receptor).

The major hypothalamic secretagogues for ACTH (adrenocorticotrophic hormone) secretion in humans and rats are CRH (corticotropin releasing hormone) and AVP (arginine vasopressin). AVP is synthesized in two classes of neurones in the hypothalamic paraventricular nucleus: magnocellular neurones that project to the posterior pituitary gland (the source for circulating AVP), and parvocellular neurones that project to the external zone of the median eminence. AVP released from the median eminence into the hypophysial portal blood directly stimulates ACTH secretion and amplifies the CRH induced secretion of ACTH. The receptor, on anterior pituitary corticotropic cells, which couples AVP to ACTH secretion has been classified as a V1b (or V3) subtype, since it has a low affinity for V1a and V2 antagonists.

CRH and AVP produce a synergistic ACTH secretory response when given together to animals (Plotsky, J Neuroendocrinol, 3,1–9, 1991) and humans (De Bold et al., J Clin Invest, 73, 533–538, 1984). The mechanism of this synergy may depend on corticotrope populations, some of which require both secretagogues for ACTH release (Jia et al, Endocrinology, 128, 197–203, 1991; Schwartz & Chenry, Endocr Rev, 13, 453–475, 1992), or on coupling between the corticotrope intracellular signalling mechanisms for the secretagogues (Abou-Sara et al, J Biol Chem, 262, 1129–1136, 1987). Once ACTH reaches the circulation it will stimulate glucocorticoid secretion (principally cortisol in human and corticosterone in rat) from the adrenal glands.

Abnormally elevated hormonal activity in the hypothalamic-pituitary-adrenal axis (the 'HPA axis') in man results in an over-secretion of ACTH causing hypercortisolaemia which thereby predisposes to a metabolic syndrome characterised by insulin resistance, hyperinsulinaemia, impaired glucose tolerance, dystipidaemia (comprising hypertriglyceridaemia, increased LDL/HDL ratio), obesity and non-insulin-dependent diabetes mellitus (NIDDM).

It is known that AVP V1a receptors (which are found predominantly on the liver and vascular tissue) and AVP V2 receptors (which are found predominantly on kidney tissue) mediate the pressor and antidiuretic actions of AVP, respectively, and have no effect on ACTH release. Peptide and non-peptide antagonists of the V1a and V2 receptor subtypes are known and have antihypertensive and diuretic actions, respectively.

The human AVP V1b receptor is known and has been cloned (J Biol Chem 269,27089–27092,1994). There are no reported non-peptidic antagonists which are specific for tie AVP V1b receptor although non-selective AVP antagonists are known (Acta Endocrinologica, 123,622–628, 1990).

Although it is known that non-selective peptide AVP antagonists can produce an effect upon the ACTH and cortisol response to exogenous AVP in normal subjects (Acta Endocrinologica, 123,622–628,1990 ), there is no reported link between this activity and the treatment or normalisation of abnormally elevated ACTH release.

It is now indicated that abnormally elevated ACTH release can be normalised by blocking AVP V1b receptors, thereby reducing the hypercortisolaemia and hence addressing a major underlying cause of the said metabolic syndrome.

Accordingly, the present invention provides a method for normalising abnormally elevated ACTH release in mammals, such as humans, which method comprises the administration of an effective, non-toxic amount of a compound which regulates the biological activity of the arginine vasopressin V1b receptor, (the AVP V1b receptor).

Abnormally augmented ACTH release in man causes hypercortisolaemia.

Hypercortisolaemia is associated with the metabolic syndrome characterised by insulin resistance, hyperinsulinaemia, impaired glucose tolerance, dyslipidaemia (comprising hypertriglyceridaemia and an increased LDL/HDL ratio), and disease states caused by these disorders.

Examples of such disease states are Type II diabetes, hypertension, atherosclerosis and obesity.

A particular disease state is Type II diabetes.

A particular disease state is obesity, especially abdominal obesity.

A particular compound which regulates the biological activity of the AVP V1b receptor is a compound which inhibits the biological activity of the AVP V1b receptor, such as an AVP V1b receptor antagonist.

A suitable antagonist is one which binds at or near the active site of the receptor thereby denying access to that receptor by the natural ligand or otherwise prevents agonist activity.

Particular antagonists include non-peptide and peptide molecules.

When used herein the term 'hypothalamic-pituitary-adrenal axis' or 'HPA axis' means a neuroendocrine axis.

In a further aspect, the present invention provides a compound which regulates the biological activity of AVP V1b receptors, for use in the treatment of conditions associated with abnormally elevated ACTH release, such as the metabolic syndrome characteristic of Type II diabetes and obesity.

In yet a further aspect, the present invention provides the use of a compound which regulates the biological activity of the AVP V1b receptor for the manufacture of a medicament for the treatment of conditions associated with abnormally elevated ACTH release, such as the metabolic syndrome characteristic of Type II diabetes and obesity.

Antagonist substances may be identified by selecting those substances which antagonise the biological activity of a V1b agonist, such as AVP, at the AVP V1b receptor in a cell line, for example a Chinese hamster ovary (CHO) cell line, stably expressing the human AVP V1b receptor.

An example of an in vitro screen involves determining the effect of a potential AVP V1b receptor antagonist upon the inhibition of inositol phosphate production generated by AVP and causing a dextral shift of the AVP displacement curve, such screen also forms a part of the present invention.

The particular compound used may be prepared by any appropriate method. For example when the compound is as disclosed in the abovementioned publications, then the methodology disclosed therein may be used.

A compound which regulates the biological activity of the AVP V1b receptor may be administered per se or, preferably, as a pharmaceutical composition also comprising a pharmaceutically acceptable carrier.

Accordingly, the present invention also provides a pharmaceutical composition comprising a compound which regulates the biological activity of the AVP V1b receptor and a pharmaceutically acceptable carrier therefor.

A compound which regulates the biological activity of the AVP V1b receptor is also considered to be part of the present invention.

Hereafter a compound which regulates biological function of the AVP V1b receptor will be referred to as 'a compound of the invention'.

As used herein the term 'pharmaceutically acceptable' embraces compounds, compositions and ingredients for both human and veterinary use.

Suitable non-human mammals include dogs and cats.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycoliate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

Conveniently, the compound of the invention may be administered as a pharmaceutical composition hereinbefore defined, and this forms a particular aspect of the present invention.

In the treatment of conditions associated with Type II diabetes, the compound of the invention may be taken in doses, such as those described above, one to six times a day In a manner such that the total daily dose for a 70 kg adult will generally be in the range of from 0.1 to 6000 mg, and more usually about 1 to 1500 mg.

The following Experiments illustrate the invention but do not limit it in any way.

Experiments Supporting the Contribution of AVP V1b Receptors to the Regulation of the Hypothalamic-pituitary-adrenal Axis in Diabetes Mellitus Experiment 1

Using the ob/ob mouse as an animal model of diabetes and obesity: Male obese (ob/ob) and lean (+/?) mice (6–7 wks old) are supplied by Harlan Olac (U.K). After 7 days of adaptation to the Animal Unit, under general anaesthesia, an osmotic minipump is implanted subcutaneously to deliver a peptidic, non-selective AVP receptor antagonist [β-Mercapto-β,β-cyclopenta-methylenepropionyl,O-Et-Tyr$^2$,Val$^4$,Arg$^8$]-AVP (Sigma) 2 μg/1 μl/h or vehicle 1 μl/h for 7 days. An oral glucose tolerance test (2 g/kg glucose[10 ml/kg], orally) is performed in 5 h fasted animals, also blood samples are collected to measure blood glucose and plasma insulin and corticosterone or ACTH concentrations.

Experiment 2

Using the db/db mouse as an animal model of diabetes and obesity: Male obese (db/db) and lean (+/?) mice (6–7 wks old) are supplied by Harlan Olac (U.K). After 7 days of adaptation to the Animal Unit, under general anaesthesia, an osmotic minipump is implanted subcutaneously to deliver a peptidic, non-selective AVP receptor antagonist [β-Mercapto-β,β-cyclopenta-methylenepropionyl,O-Et-Tyr$^2$,Val$^4$,Arg$^8$]-AVP (Sigma) 2 μg/1 μl/h or vehicle 1 μl/h for 7 days. An oral glucose tolerance test (2 g/kg glucose[10 ml/kg], orally) is performed in 5 h fasted animals, also blood samples are collected to measure blood glucose and plasma insulin and corticosterone or ACTH concentrations.

Experiment 3

Streptozotocin (STZ) induced diabetes in rats: male Sprague-Dawley rats (280–300 g) are supplied by Charles River (U.K). After 7 days of adaptation to the Animal Unit, rats are treated with streptozotocin (STZ, 55–65 mg/kg,i.v.). A small blood sample is collected by cutting the tip of the tail to assess the development of hyperglycaemia. Following 1 to 2 weeks of STZ-induced diabetes, either jugular or femoral vein is cannulated under general anaesthesia and connected to an osmotic minipump to infuse a peptidic, non-selective AVP receptor antagonist [β-Mercapto-β,β-cyclopenta-methylenepropionyl,O-Et-Tyr$^2$,Val$^4$,Arg$^8$]-AVP (Sigma) 2 μg/1 μl/h or vehicle 1 μl/h for 7 days. An oral glucose tolerance test (2 g/kg glucose[10 ml/kg], orally) is performed in 5 h fasted animals; also blood samples are collected to measure blood glucose, and plasma insulin, corticosterone and ACTH concentrations.

Experiment 4

Using Zucker (fa/fa) rats, an animal model of obesity and insulin resistance: male fa/fa and Fa/? Zucker rats (6–7 wks old) are supplied by Harlan Olac (U.K). After 7 days of adaptation to the Animal Unit, under general anaesthesia, either a femoral or jugular vein is cannulated and connected to an osmotic minipump to deliver a peptidic, non-selective AVP receptor antagonist [β-Mercapto-β,β-cyclopenta-methylenepropionyl,O-Et-Tyr$^2$,Val$^4$,Arg$^8$]-AVP (Sigma) 2 μg/1 μl or vehicle 1 μl/h for 7 days. An oral glucose tolerance test (2 g/kg glucose[10 ml/kg], orally) is performed in 5 h fasted animals; also blood samples are collected to measure blood glucose, and plasma insulin, corticosterone and ACTH concentrations.

Experiment 5

A study was performed in 4–6 weeks old C57BL/6J mice homozygous (ob/ob) for the obese gene mutation to assess the effect of [deamino-Pen$^1$, o-Me-Tyr$^2$, Arg$^8$]-AVP (Sigma) a non-selective peptide V1b receptor antagonist on corticosterone concentration. Osmotic minipumps (Alzet Model 1007D, 0.5 μl/h for 7 days) were filled either with the peptide (to deliver 86.4 μg/day for 7 days) or vehicle and primed at least for 4 h at 37° C. before their implantation. A group of mice heterozygous (+/?) for the obese gene mutation was also implanted with osmotic minipumps filled with vehicle alone. After 7 days of treatment blood was collected into EDTA tubes and separated plasma assayed for corticosterone concentration measurement, by using a commercial rat $^{125}$I-corticosterone (Amersham, U.K.).

Plasma corticosterone concentration was reduced in ob/ob mice treated with V1a/V1b antagonist (AVP antagonist 109.9±19.4 ng/ml vs vehicle 228.9±63 ng/ml, n=7 per group), and reached a level similar to that of lean (ob/?) group (123.2?24.3 ng/ml, n=8). The data support the hypothesis that an antagonist of vasopressin V1b receptor normalises the abnormally elevated HPA axis in animal model of obesity and diabetes.

We claim:

1. A method for the treatment of hypercortisolaemia, Type II diabetes, hypertension, atherosclerosis or obesity in mammals, which method comprises the administration of an effective, non-toxic amount of an arginine vasopressin V1b receptor (the AVP V1b receptor) antagonist.

2. A method according to claim 1 for the treatment of abdominal obesity.

3. A method according to claim 1 wherein the antagonist is a non-peptide or a peptide molecule.

4. A method according to claim 2 wherein the antagonist is a non-peptide or a peptide molecule.

* * * * *